United States Patent [19]

Jessel, Jr. et al.

[11] Plant 4,401

[45] Mar. 27, 1979

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 903,034

[22] Filed: May 4, 1978

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A chrysanthemum plant known by the cultivar name Quills and particularly characterized as to uniqueness by the combined characteristics of flat capitulum form; spooned daisy capitulum type; white ray floret color, devoid of pink discoloration; diameter across face of capitulum ranging from 65 to 100 mm. at maturity; uniform seven week photoperiodic flowering response to short days; medium plant height when grown as a pinched spray pot; semi-upright branching pattern, and minimum pollen production.

1 Drawing Figure

The present invention comprises a new and distinct cultivar of *Chrysanthemum morifolium,* Ramat., hereinafter referred to by the cultivar name Quills (#75179121).

Quills is a product of a planned breeding program which had the objective of creating new chrysanthemum cultivars with spooned daisy capitulum type, with white ray floret color, with seven or eight week flowering response, and with the ability to produce commercially acceptable quality in year round pot mum programs. Such traits in combination were not present in previously available commercial cultivars.

Quills was originated from a cross made in a controlled breeding program in Barberton, Ohio in 1974. The female parent was #73116030 (unnamed seedling), a white spooned daisy originated by the present inventors from a cross between #70025007 (unnamed seedling) and Neptune (#60228001; unpatented; commercially available). The male parent of Quills was #71388001 (unnamed seedling), a white spooned daisy originated by the present inventors from a cross between White Spider Pot 2275 (#66506001; unpatented; commercially available) and Illini Spinwheel (#68508002; U.S. Plant Pat. No. 3,379; commercially available). #70025007 and Neptune are products of the breeding program of the present inventors. White Spider Pot 2275 and Illini Spinwheel are of parentage unknown to the present inventors.

Quills was discovered and selected as one flowering plant within the progeny of the stated cross by Walter H. Jessel, Jr. and William E. Duffett on Nov. 20, 1975 in a controlled environment in Barberton, Ohio.

The first act of asexual reproduction of Quills was accomplished when vegetative cuttings were taken from the initial selection in February 1976 in a controlled environment in Barberton, Ohio, by a technician working under formulations established and supervised by Walter H. Jessel, Jr. and William E. Duffett. Horticultural examination of selected units initiated Oct. 4, 1976 has demonstrated that the combination of characteristics as herein disclosed for Quills are firmly fixed and are retained through successive generations of asexual reproduction.

Quills has not been observed under all possible environmental conditions. The phenotype may vary significantly with variations in environment such as temperature, light intensity, and daylength. The following observations, measurements, and comparisons describe plants grown in Barberton, Ohio under greenhouse conditions which approximate those generally used in commercial practice.

The following traits have been repeatedly observed and are determined to be basic characteristics of Quills which in combination distinguish this chrysanthemum as a new and distinct cultivar:

(1) Flat capitulum form.

(2) Spooned daisy capitulum type.

(3) White ray floret color, devoid of pink discoloration.

(4) Yellow-green (immature) to yellow (mature) disc floret color.

(5) Diameter across face of capitulum ranging from 65 to 100 mm. at maturity.

(6) Uniform seven week photoperiodic flowering response to short days.

(7) Medium plant height (requiring 1–2 long day weeks prior to pinch and short days, and one application 2500 ppm B-9 SP 14 to 21 days after the beginning of short days to attain a flowered plant height of 30 to 45 cm.

(8) Semi-upright branching pattern.

(9) Minimum pollen production.

The accompanying photographic drawings show typical inflorescence and foliage characteristics of Quills, with colors being nearly as true as possible with illustrations of this type. Sheet 1 is a color photograph of Quills. Sheet 2 is a black and white photograph showing three views of the inflorescence of Quills. Sheet 3 is a black and white photograph showing the foliage of Quills at three stages of growth.

Of the many commercial cultivars known to the present inventors, the most similar existing cultivar in comparison to Quills is the cultivar Illini Spinwheel. Reference is made to attached Chart A which compares certain characteristics of Quills to those same characteristics of Illini Spinwheel. General comparisons are as follows:

In comparison to Illini Spinwheel, Quills has less tendency to discolor its ray florets with pink tinging under cool (less than 60° F.) finishing temperatures and with maturity; produces less pollen; has larger capitulum size, and earlier flowering response. The ray floret color at finishing temperature of 60° F. and warmer; capitulum form; capitulum type, and plant height of Quills are similar to those of Illini Spinwheel.

In the following description, color references are made to The Munsell Color Cascade, 1972 edition. The color values were determined between 10:00 and 10:30 A.M. on Feb. 24, 1978 under 100 foot-candle light intensity at Salinas, Calif.

Botanical classification: *Chrysanthemum morifolium,* Ramat., cv Quills.

*Androecium.*—Present disc florets only; scant to numerous; scant pollen.

*Gynoecium.*—Present both ray and disc florets.

D. Corolla of disc florets:

*Color.*—20-10 (immature) to 26-4 (mature).

II. PLANT

A. General appearance: semi-upright branching pattern, medium height.

B. Foliage: (See Sheets 1 and 3).

*Color (abaxial).*—Approximately 21-14 to 22-14.

*Color (adaxial).*—Approximately 21-13 overlaid with white.

CHART A

COMPARISON OF QUILLS AND ILLINI SPINWHEEL

| CULTIVAR | RAY FLORET COLOR | CAPITULUM FORM AND TYPE | POLLEN PRODUCTION | DIAMETER ACROSS FACE OF CAPITULUM | PLANT HEIGHT | FLOWERING RESPONSE PERIOD |
|---|---|---|---|---|---|---|
| Quills | White | Flat spooned daisy | Sparse | 65 to 100 mm. | Medium | 7 week |
| Illini Spinwheel | White, tinging pink with cool temperatures and age. | Flat spooned daisy | Abundant | 45 to 60 mm. | Medium | 8 week |

COMPARISONS MADE OF PLANTS GROWN AS PINCHED SPRAY POTS IN BARBERTON, OHIO.

I. INFLORESCENCE

A. Capitulum: (See Sheets 1 and 2 of drawings).

*Form.*—Flat.

*Type.*—Spooned daisy.

*Diameter across face.*—65 to 100 mm.

B. Corolla of ray florets:

*Persistence.*—Resists shatter.

*Color (abaxial).*—White.

*Color (adaxial).*—White.

C. Reproductive organs:

We claim:

1. A new and distinct cultivar of *Chrysanthemum morifolium,* Ramat., plant known by the cultivar name Quills and particularly characterized as to uniqueness by the combined characteristics of flat capitulum form; spooned daisy capitulum type; white ray floret color, devoid of pink discoloration; diameter across face of capitulum ranging from 65 to 100 mm. at maturity; uniform seven week photoperiodic flowering response to short days; medium plant height when grown as a pinched spray pot; semi-upright branching pattern; and minimum pollen production.

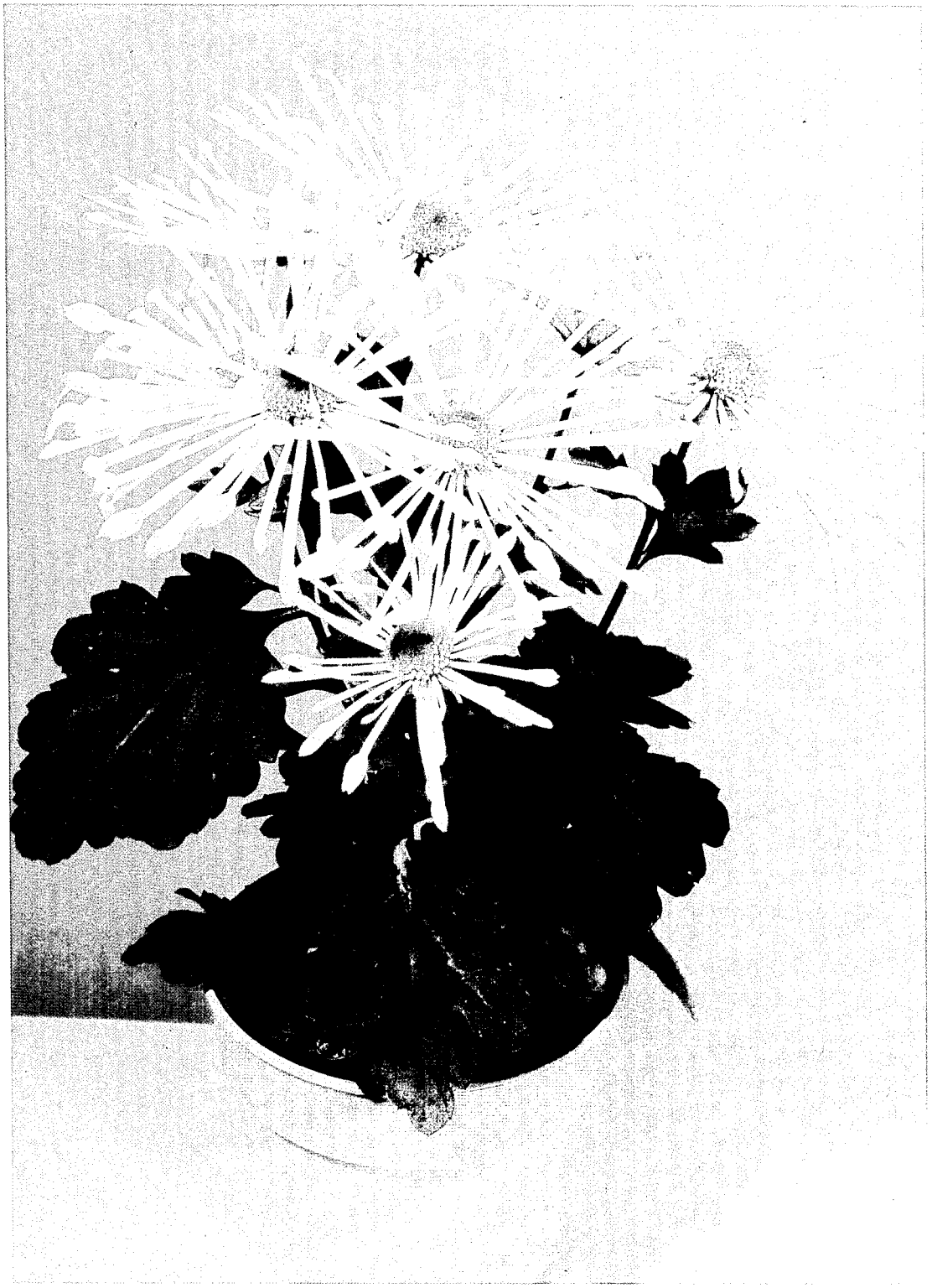

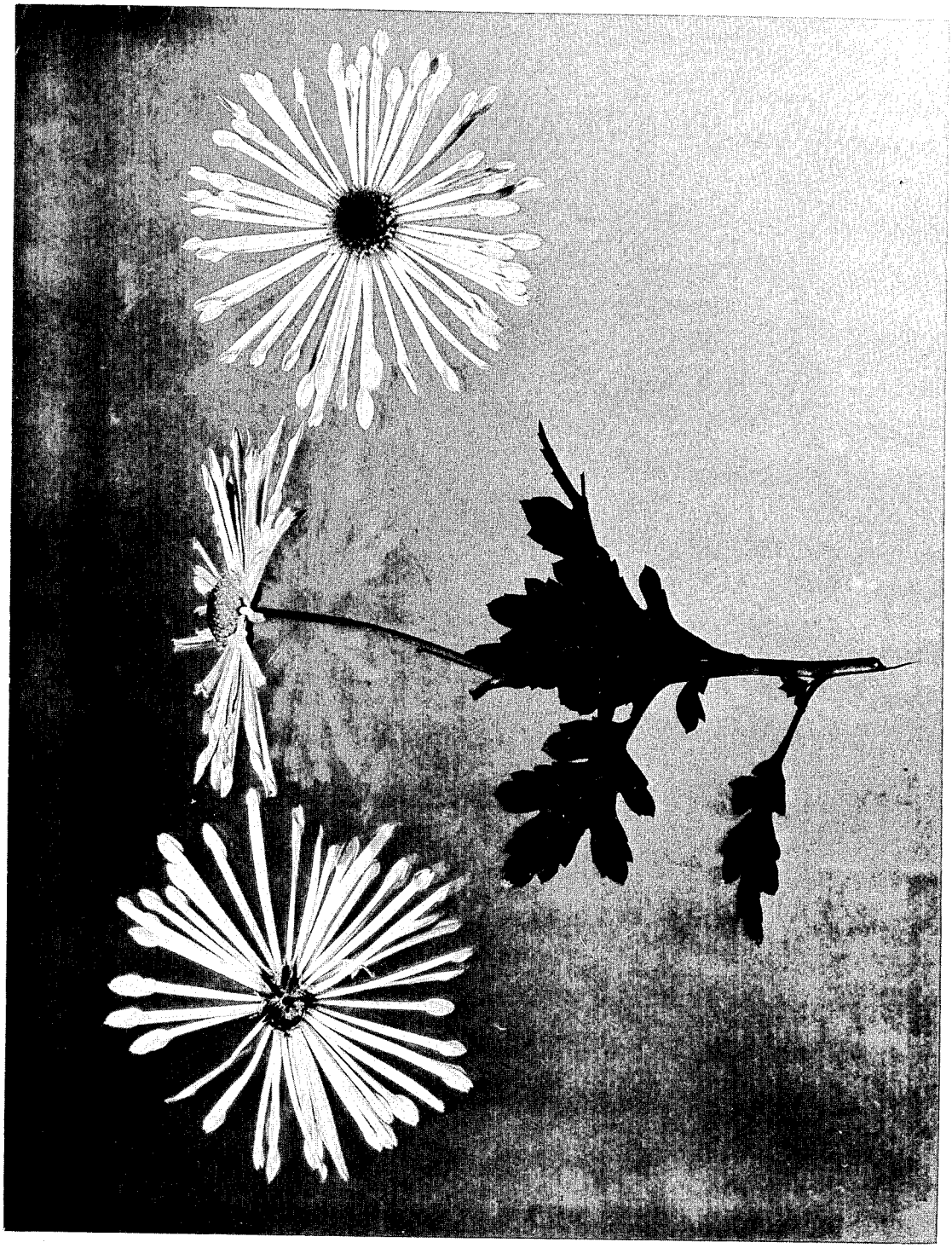

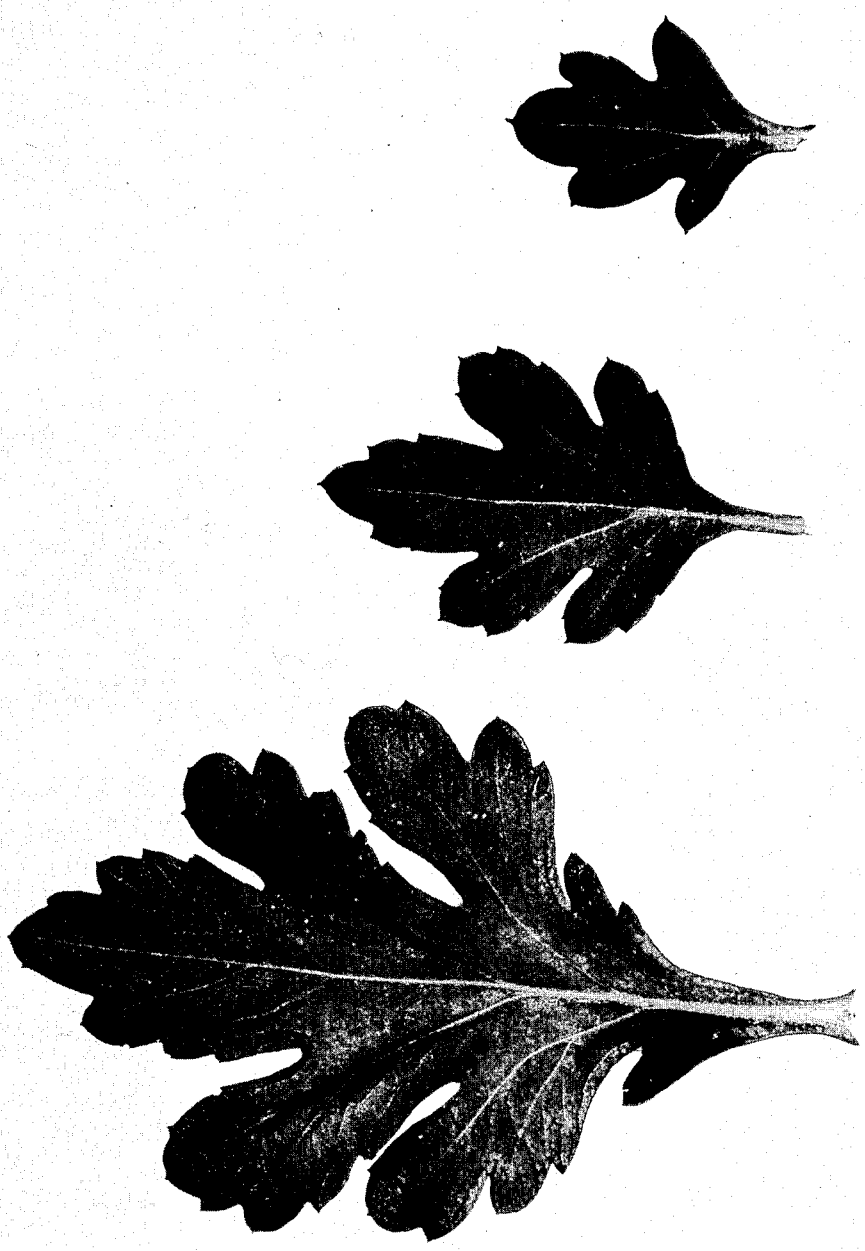

* * * * *